United States Patent [19]

Hebeisen

[11] Patent Number: 4,888,429

[45] Date of Patent: Dec. 19, 1989

[54] PROCESS FOR PRODUCING ALLYL AMINOTHIAZOLE ACETATE INTERMEDIATES

[75] Inventor: Paul Hebeisen, Reinach, Switzerland

[73] Assignee: Hoffmann-La Roche Inc., Nutley, N.J.

[21] Appl. No.: 258,062

[22] Filed: Oct. 17, 1988

Related U.S. Application Data

[63] Continuation of Ser. No. 807,702, Dec. 11, 1985, abandoned.

[30] Foreign Application Priority Data

Dec. 19, 1984 [CH] Switzerland ................ 6008/84

[51] Int. Cl.$^4$ ............................................ C07D 277/40
[52] U.S. Cl. .................................................. 548/194
[58] Field of Search ........................................ 548/194

[56] References Cited

U.S. PATENT DOCUMENTS 4,598,154  7/1986  Oine ................................. 548/194
4,652,651  3/1987  Furlenmeier et al. .

FOREIGN PATENT DOCUMENTS 96297  12/1983  European Pat. Off. .
96926  12/1983  European Pat. Off. .

OTHER PUBLICATIONS

Greene, Protective Groups in Organic Synthesis, pp. 169-170 (1981).
March Advanced Organic Chemistry, 3rd Ed., pp. 351-352 (1985).
Patai, The Chem. of Carboxylic Acids and Esters, pp. 109-115 (1969).
Furleinmeier et al., Chem. Abst. 100:174525y (1984).
Furleinmeier et al., Chem. Abst. 100:191650c (1984).
Ser. No. 499,971, to Furlenmeier et al., Filed 6/1/83.

Primary Examiner—Robert Gerstl

Attorney, Agent, or Firm—Jon S. Saxe; Bernard S. Leon; A. Kate Huffman

[57] ABSTRACT

There is described a process for the manufacture of a compound of the formula

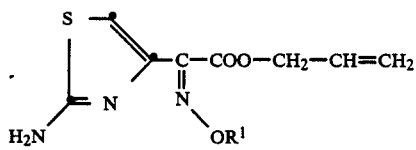

wherein $R^1$ is lower alkyl, lower alkanoyl, lower alkenyl or the group $-CH_2COOR^2$ or $-C(CH_3)_2COOR^2$ and $R^2$ is a readily cleavable group, by reacting a compound of the formula

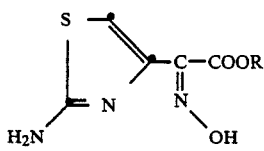

wherein R is lower alkyl, with an alkali metal allylate and reacting the resulting compound of the formula

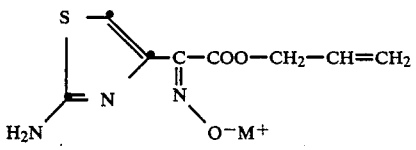

wherein M is an alkali metal atom, with a compound of the formula $R^1$-X, wherein X is a leaving group. This process can be used to manufacture antimicrobially active mono-β-lactam, cephalosporin and penicillin derivatives.

6 Claims, No Drawings

PROCESS FOR PRODUCING ALLYL AMINOTHIAZOLE ACETATE INTERMEDIATES

This application is a continuation of application Ser. No. 807,702, filed Dec. 11, 1985 now abandoned.

BACKGROUND OF THE INVENTION

This invention relates to a process for producing allyl aminothiazole acetate intermediates which can be converted to antimicrobially active mono-β-lactam, cephalosporin and penicillin derivatives.

SUMMARY OF THE INVENTION

The present invention concerns a process for producing a compound of the formula

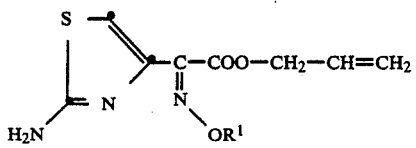

IV wherein $R^1$ is lower alkyl, lower alkanoyl, lower alkenyl, $-CH_2COOR^2$ or $-C(CH_3)_2COOR^2$, and $R^2$ is a readily cleavable group.

In accordance with the inventive process, a compound of the formula

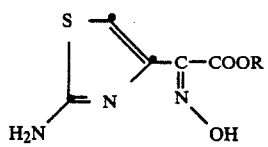

II wherein R is lower alkyl, is reacted with an alkali metal allylate, and the resulting compound of the formula

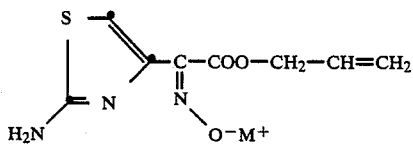

I wherein M is an alkali metal atom, is reacted with a compound of the formula

V wherein X is a leaving group, thereby to produce compound IV.

Compound IV is an intermediate which is useful for producing antimicrobially active mono-β-lactam, cephalosporin and penicillin derivatives, whose amino group on the β-lactam ring is substituted with a group of the formula

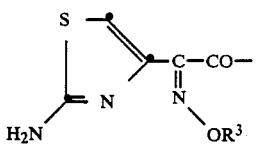

(Q)

wherein $R^3$ is hydrogen, lower alkyl, lower alkenyl, $-CH_2COOR^4$ or $-C(CH_3)_2COOR^4$, and $R^4$ is hydrogen or a group readily removable by hydrolysis.

DETAILED DESCRIPTION OF THE INVENTION

The present invention is concerned with a process for producing a compound of the formula

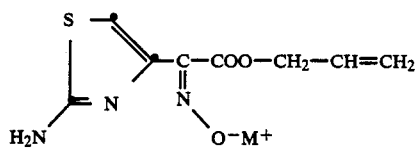

I wherein M is an alkali metal atom, which process comprises reacting a compound of the formula

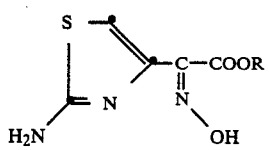

II wherein R is lower alkyl, with a compound of the formula

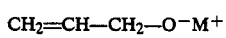

$$CH_2=CH-CH_2-O^-M^+$$

wherein M has the above significance, under anhydrous conditions and in a solvent of allyl alcohol.

The present invention is also concerned with a process for producing a compound of the formula

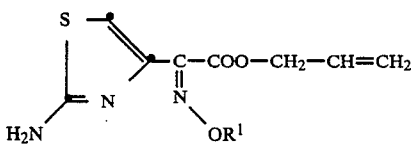

IV wherein $R^1$ is lower alkyl, lower alkanoyl, lower alkenyl, $-CH_2COOR^2$ or $-C(CH_3)_2COOR^2$, and $R^2$ is a readily cleavable group, which process comprises reacting a compound of formula I obtained in accordance with the invention with a compound of the formula

V wherein x is a leaving group and $R^1$ has the above significance, thereby to produce compound IV.

The invention also is concerned with the use of these processes for the manufacture of antimicrobially active mono-β-lactam, cephalosporin and penicillin derivatives, whose amino group on the β-lactam ring is substituted with a group of the formula

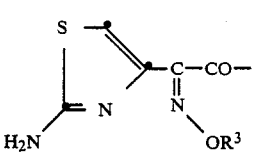

(Q)

wherein R³ is hydrogen, lower alkyl, lower alkenyl, —CH₂COOR⁴ or —C(CH₃)₂COOR⁴ and R⁴ is hydrogen or a group readily removable by hydrolysis.

The term "lower" denotes residues and compounds with a maximum of 7, preferably a maximum of 4, carbon atoms. The term "alkyl" denotes straight-chain or branched, saturated hydrocarbon residues of 1 to 7 carbon atoms such as methyl, ethyl and s-butyl. The term "alkenyl" denotes straight-chain or branched, unsaturated hydrocarbon residues of 3 to 7 carbon atoms such as allyl, 2-butenyl and 3-butenyl. The term "alkanoyl" denotes straight-chain or branched fatty acid residues of 1 to 7 carbon atoms. More particularly, "alkanoyl" denotes moieties derived from alkanecarboxylic acid derivatives such as acetyl, propanoyl and isobutyryl.

The term "halogen" denotes chlorine, bromine and iodine. The term "alkali metal" includes lithium, sodium and potassium. The term "lower alkoxy" denotes alkoxy groups of 1 to 7 carbon atoms. The term "lower alkanoyloxy-lower alkyl group" denotes moieties wherein their alkyl portion is defined as above and their alkanoyloxy portion denotes alkanoyl moieties attached via an oxygen atom.

The term "aryl" includes mononuclear aromatic hydrocarbon groups which an be unsubstituted or substituted in one or more positions with halogen, lower alkyl or lower alkoxy. Suitable mononuclear aromatic hydrocarbon groups are phenyl and the like.

The term "readily cleavable group" denotes any conventional moiety which is cleavable under mild conditions. The term preferably denotes a benzyl group unsubstituted or optionally substituted on the phenyl ring by halogen, lower alkoxy or nitro, such as benzyl, p-nitrobenzyl, p-methoxybenzyl, 2,4- or 3,4-dimethoxybenzyl and p-chlorobenzyl, t-alkyl groups, such as t-butyl, lower alkyl groups halogenated in the 2-position, such as 2,2,2-trichloroethyl, 2-bromoethyl and 2-iodoethyl, lower alkyl groups silylated in the 2-position, such as 2-trimethylsilylethyl, and groups which are readily removable by hydrolysis.

A group readily removable by hydrolysis denotes any conventional group which is removable by hydrolysis under physiological conditions. More particularly, it includes any conventional radical which is cleavable under neutral, mildly acidic or mildly basic conditions or a conventional group cleavable enzymatically. There especially is preferred lower alkanoyloxy-lower alkyl groups, such as the acetoxymethyl, pivaloyloxymethyl, 1-acetoxyethyl and the 1-pivaloyloxyethyl group, and lower alkoxycarbonyloxy-lower alkyl groups, such as the methoxycarbonyloxymethyl, 1-ethoxycarbonyloxyethyl and the 1-isopropoxycarbonyloxyethyl group.

The term "leaving group" denotes any conventional leaving group which is removable to permit the reaction of compound I with compound V. Among the suitable groups are sulphonyloxy groups and halogen atoms. Suitable sulphonyloxy groups are, for example, lower alkylsulphonyloxy groups, such as the methanesulphonyloxy group, and arylsulphonyloxy groups, such as the p-toluenesulphonyloxy group. Suitable halogen atoms are, for example, the chlorine, bromine and iodine atom.

The transesterification reaction in accordance with the invention of a compound of formula II with an alkali metal allylate of formula III can be carried out in a wide temperature range, for example in a range of about 0° C. to about the boiling temperature of the reaction mixture. However, the reaction is conveniently carried out at room temperature (about 23° C.) As the starting material of formula II there is preferably used the corresponding ethyl ester, a commercially available compound. Potassium allylate is preferably used as the starting material of formula III. The reaction occurs under anhydrous conditions and preferably the solvent essentially consists of allyl alcohol.

The alkali metal allylates of formula III can be prepared by reacting allyl alcohol with a base such as alkali metals, alkali metal hydrides, such as sodium hydride, alkali metal alkyls, such as n-butyl lithium, or alkali metal hydroxides, such as potassium hydroxide, according to methods known per se. One thus obtains a solution of a corresponding allyl alcohol salt of formula III in allyl alcohol. If desired, compound II then can be added to this solution to produce compound I.

In order to carry out the reaction of a compound of formula I obtained in accordance with the invention with a compound of formula V, the compound of formula I is conveniently suspended or dissolved in an inert organic solvent. Suitable solvents are, for example, hydrocarbons, such as pentane, hexane, cyclohexane, petroleum ether, benzene, toluene and xylene, ethers, such as tetrahydrofuran, dioxan, ethylene glycol dimethyl ethr, diethyl ether and t-butyl methyl ether, N,N-dimethylformamide, acetone, ethyl acetate, acetonitrile and dimethyl sulphoxide. The reaction can be carried out in a wide temperature range, for example in a range of about 0° C. to the boiling temperature of the reaction mixture. As the starting material of formula V there is preferably used the corresponding halide.

As already mentioned, the processes in accordance with the invention can be used for the manufacture of antimicrobially active mono-β-lactam, cephalosporin and penicillin derivatives, whose amino group on the β-lactam ring is substituted with a group of formula Q. The compounds of formula IV belong to a class of substance which is known per se and can be converted into the desired, antimicrobially active mono-β-lactams, cephalosporins and penicillins in analogy to the known representatives of this class of substance.

The following Examples, which illustrate the present invention, but are not intended to be limiting in any manner, also contain detailed information concerning the use of the processes in accordance with the invention for the manufacture of the aforementioned antimicrobially active end products. All temperatures are given in degrees Celsius (°C.) and room temperature is about 23° C. Unless otherwise indicated, the Examples were carried out as written.

EXAMPLE 1

(a) 33.7 g (600 mmol) of potassium hydroxide are dissolved in 200 ml of allyl alcohol, 300 ml of toluene are added thereto, the slightly turbid solution is filtered and the filtrate is concentrated at 30° C. in vacuo (removal of water). The oily residue is taken up again in 300 ml of toluene and the solution is again concentrated in vacuo. The potassium allylate obtained is dissolved in 900 ml of allyl alcohol, whereupon the solution is treated with 64.5 g (300 mmol) of ethyl 2-(2-amino-4-thiazolyl)-2-syn-hydroxyimino-acetate and the mixture is stirred at room temperature for 2 days. The crystallized-out material is filtered off under suction, washed in succession with allyl alcohol, ethyl acetate and ether and dried at 40° C. in vacuo. There is obtained the potassium salt of allyl 2-(2-amino-4-thiazolyl)-2-syn-hydroxyimino-acetate of m.p. >250° C.

(b) 76.2 g (287.2 mmol) of the potassium salt of allyl 2-(2-amino-4-thiazolyl)-2-syn-hydroxyimino-acetate are suspended in 1.4 l of tetrahydrofuran, the suspension is cooled to 0° C. and treated while stirring with 20.4 ml (287.2 mmol) of acetyl chloride. After 1 hour the mixture is concentrated to a small volume and treated with 3 l of ethyl acetate. The solution obtained is washed three times with water and the aqueous extracts are shaken out with 1 l of ethyl acetate. The dark colored organic phase is treated with animal charcoal, dried over magnesium sulphate and evaporated in vacuo. The residue is taken up in 1 l of methylene chloride, filtered in order to remove undissolved material, then treated with 2 l of carbon tetrachloride and concentrated to a small volume. The crystallized-out material is filtered off under suction, washed with carbon tetrachloride and petroleum ether and dried at 40° C. in vacuo. There is obtaned allyl 2-(2-amino-4-thiazolyl)-2-syn-acetoxyimino-acetate of m.p. 144°–147° C.

(c) 54 g (200 mmol) of allyl 2-(2-amino-4-thiazolyl)-2-syn-acetoxyimino-acetate are dissolvd in 1.4 l of acetonitrile under nitrogen, the solution is cooled to 0° C. and treated in succession with 448 mg (2 mmol) of palladium(II) acetate and 1.72 ml (10 mmol) of triethyl phosphite. After 5 minutes 23.2 ml (220 mmol) of N-methylpyrrolidine are added thereto and the mixture is stirred at 0° C. overnight and under nitrogen, whereby the N-allyl-N-methylpyrrolidinium salt of 2-(2-amino-4-thiazolyl)-2-syn-acetoxyimino-acetic acid crystallizes out.

(d) Subsequently, there are added thereto 28 ml (248 mmol) of N-methylmorpholine and after 30 minutes 74 g (220 mmol) of 2,2-dithio-bis-benzothiazole. Within 4 hours there is then added dropwise thereto at 0° C. while stirring a solution of 42 ml (245 mmol) of triethyl phosphite in 200 ml of acetonitrile. The mixture is subsequently stirred for a further 30 minutes. The crystallized-out material is filtered off under suction, washed firstly with acetonitrile and then with ether and dried at 30° C. in vacuo. There is obtained 2-(2-amino-4-thiazolyl)-2-syn-acetoxyimino-acetic acid 2-benzthiazolyl thioester of m.p. 170°–172° C.

(e) 29.6 g (80 mmol) of 7-amino-3-{[(2,5-dihydro-6-hydroxy-2-methyl-5-oxo-as -3-triazinyl)thio]methyl}-3-cephem-4-carboxylic acid are suspended in 56 ml of N,N-dimethylformamide, the suspension is treated with 24.8 ml (176 mmol) of triethylamine, the mixture is cooled to 0° C. and 80 ml of water are added thereto. To the clear solution obtained there are added 38 g (100 mmol) of 2-(2-amino-4-thiazolyl)-2-syn-acetoxyiminoacetic acid 2-benzthiazolyl thioester in solid form and the reaction mixture is stirred at 0° C. for 3 hours. The dark solution is filtered, and the residue is washed twice with 40 ml of N,N-dimethylformamide each time. The solution is cooled to 0° C., treated with 96 ml (192 mmol) of a 2N solution of sodium 2-ethylcaproate in ethyl acetate, 1080 ml of acetone are added thereto at 0° C. within 30 minutes and while stirring, the precipitated material is filtered off under suction, washed firstly with 500 ml of a mixture of acetone and N,N-dimethylformamide in the ratio 3:2 by volume and then with 500 ml of acetone and dried at room temperature in vacuo. There is obtained the disodium salt of 7-[2-(2-amino-4-thiazolyl)-2-syn-acetoxyiminoacetamido]-3-{[(2,5-dihydro-6-hydroxy-2-methyl-5-oxo-as -3-triazinyl)-thio]methyl}-3-cephem-4-carboxylic acid which has a degree of purity of 96.6% in accordance with HPLC.

(f) 48 g (76.6 mmol) of the disodium salt of 7-[2-(2-amino-4-thiazolyl)-2-syn-acetoxyiminoacetamido]-3-{[(2,5-dihydro-6-hydroxy-2-methyl-5-oxo-as -3-triazinyl)thio]methyl}-3-cephem-4-carboxylic acid are dissolved in a solution, cooled to 25° C., of 520 ml of methanol and 400 ml of water. The pH of the solution is adjusted by means of 1N sodium hydroxide solution to 8 and held at this pH during the entire reaction duration, whereby the consumption of sodium hydroxide solution is very small. After the reaction has finished (the course of the reaction is followed by means of HPLC) the pH is adjusted to 7 with 1N hydrochloric acid and the dark colored solution is stirred for 20 minutes wit 10 g of active carbon. The mixture is subsequently filtered, and the residue is washed with a mixture of 52 ml of methanol and 40 ml of water. The yellow solution obtained is treated with 2.4 l of alcohol while stirring, whereupon the mixture is cooled to 0° C., the precipitated material is filtered off under suction, washed firstly with 350 ml of a mixture of alcohol and water (6:1 by volume) and then with 450 ml of alcohol and subsequently dried at 1600 Pa and room temperature and then in a high vacuum. There are obtained 34.7 g (77.5%) of the disodium salt of 7-[2-(2-amino-4-thiazolyl)-2-syn-hydroxyiminoacetamido]-3-{[(2,5-dihydro-6-hydroxy-2-methyl-5-oxo-as -3-triazinyl)thio]methyl}-3-cephem-4-carboxylic acid which still contains 5.9% ethanol and 4.9% water.

Microanalysis: [Calculated for $C_{17}H_{14}N_8Na_2O_7S_3$ (584.51) +5.9% ethanol +4.9% water]: Calculated: C 34.24; H 3.48; N 17.10. Found: C 33.79; J 3.20; N 17.24.

EXAMPLE 2

(a) 4.30 g of sodium hydride (99 percent) are added portionwise at 2° C. to 200 ml of allyl alcohol. After the evolution of gas has finished 40.0 g of ethyl 2-(2-amino-4-thiazolyl)-2-syn-hydroxyimino-acetate are added in one portion and the mixture is stirred at room temperature for 2 hours. Thereupon, 40 ml of solvent are distilled off in vacuo and the residue is stirred at room temperature overnight. The product is filtered off, washed with ethyl acetate and t-butyl methyl ether and dried up to constant weight in a high vacuum. There is obtained the sodium salt of allyl 2-(2-amino-4-thiazolyl)-2-syn-hydroxyimio-acetate.

(b) 62 ml of n-butyl lithium (1.6M in hexane) are added dropwise at −78° C. to 240 ml of allyl alcohol, the mixture is left to warm to room temperature and 100 ml of solvent are removed in vacuo. 21.5 g of ethyl 2-(2-amino-4-thiazolyl)-2-syn-hydroxyimino-acetate are then added thereto and the reaction mixture is stirred overnight. The product is filtered off, washed with ethyl acetate and t-butyl methyl ether and dried up to constant weight in a high vacuum. There is obtained the lithium salt of allyl 2-(2-amino-4-thiazolyl)-2-syn-hydroxyimino-acetate of m.p. >260° C.

(c) 337 g of potassium hydroxide are dissolved in 2 l of allyl alcohol while stirring, the solution is treated with 3 l of toluene and the mixture is evaporated in vacuo (2000 Pa). The mixture is again treated with 3 l of toluene and again evaporated. The residue is taken up in 9 l of allyl alcohol, whereupon the solution is treated with 645 g of ethyl 2-(2-amino-4-thiazolyl)-2-syn-hydroxy-imino-acetate and stirred at room temperature for 45 hours. The product is filtered off, washed with 1 l of allyl alcohol, 8 l of ethyl acetate and 2.5 l of t-butyl methyl ether and dried up to constant weight at 40° C. in a high vacuum. There is obtained the potassium salt of allyl 2-(2-amino-4-thiazolyl)-2-syn-hydroxyimino-acetate.

$^1$HNMR spectrum in (CD$_3$)$_2$SO: In each case signals at 9.20 (s broad, 2H); 5.96 (s, 1H); 6.3–5.0 (m, 3H); 4.66 (d, J=6.5 Hz, 2H) ppm.

EXAMPLE 3

4.60 g of the lithium salt of allyl 2-(2-amino-4-thiazolyl)-2-syn-hydroxyimino-acetate are dissolved in 20 ml of dry N,N-dimethylformamide, whereupon the solution is treated dropwise with 3.4 ml of freshly distilled allyl bromide. The temperature thereby arises to 50° C. After 15 minutes the mixture is treated with satuarted ammonium chloride solution and extracted with ethyl acetate. The combined organic phases are washed twice with water and with saturated sodium chloride solution and dried over magnesium sulphate. The residue obained after evaporation of the solvent is recrystallized from t-butyl methyl ether. There is obtained allyl 2-(2-amino-4-thiazolyl)-2-syn-allyloxyimino-acetate of m.p. 106°–107° C.

EXAMPLE 4

(a) 82 g (0.38 mol) of ethyl 2-(2-amino-4-thiazolyl)-2-syn-hydroxyimino-acetate are added to 360 ml of a solution of potassium allylate in allyl alcohol containing 0.5 mol of potassium allylate. The suspension is stirred at room temperature for 20 hours under argon, whereupon the precipitated material is filtered off under suction, washed with ethyl acetate and ether and dried at 50° C. in vacuo (1600 Pa). There is obtained the potassium salt of allyl 2-(2-amino-4-thiazolyl)-2-syn-hydroxyimino-acetate.

(b) 39.5 g of the above potassium salt are suspended in 450 ml of absolute acetone at room temperature, the suspension is treated with 5 g of potassium iodide and 26.9 g of t-butyl chloroacetate and the mixture is subsequently heated under reflux and under argon for 4 hours. Thereafter, the mixture is poured into 750 ml of ethyl acetate and 750 ml of water, stirred well, the phases are separated and the aqueous phase is washed with 400 ml of ethyl acetate. The combined ethyl acetate phases are washed with saturated sodium chloride solution, dried over sodium sulphate and evaporated. The residue is recrystallized from 540 ml of toluene, whereby there is obtained allyl 2-(2-amino-4-thiazolyl)-2-syn-[[(t-butoxycarbonyl)mehoxy]imino]-acetate of m.p. 136°–138° C.

(c) 21.5 g of allyl 2-(2-amino-4-thiazolyl)-2-syn-[[(t-butoxycarbonyl)methoxy]imino]-acetate are suspended in 150 ml of absolute acetonitrile, there are then added thereto in succession while stirring and under argon 120 mg of palladium(II) acetate, 0.5 ml of triethyl phosphite and 5.3 ml of N-methylpyrrolidine and the mixture is stirred at room temperature for about 1.5 hours, whereby the N-allyl-N-methylpyrolidinium salt of 2-(2-amino-4-thiazolyl)-2-syn-[[(t-butoxycarbonyl)methoxy]imino]-acetic acid crystallizes out. The suspension is subsequently treated with 6 ml of N-methylmorpholine and 20 g of dithio-bis-2-benzthiazole, the mixture is cooled to −5° C. to 0° C. and then a solution of 12 ml of triethyl phosphite in 30 ml of absolute acetonitrile is added dropwise thereto during 2 hous. 1 hour after completion of the addition the mixture is cooled to −10° C. and the crystalline thiol ester is filtered off under suction, washed in succession with 35 ml of acetonitrile and 35 ml of ether and dried at 60° C. in vacuo (1600 Pa). There is obtained 2-(2-amino-4-thiazolyl)-2-syn-[[(t-butoxycarbonyl)methoxy]imino]-acetic acid 2-benzthiazolyl thioester of m.p. 142°–144° C.

(d) 71.8 g (0.3 mol) of (3S,4S)-3-amino-4-carbamoyloxymethyl-2-oxo-1-azetidinesulphonic acid are dispersed in 1.5 l of methylene chloride, whereupon the dispersion is treated with stirring with 45.6 g (0.45 mol) of triethylamine and 148.6 g (0.33 mol) of 2-(2-amino-4-thiazolyl)-2-syn-[[(t-butoxycarbonyl)methoxy]imino]acetic acid 2-benzthiazolyl thioester. The reaction mixture is stirred at room temperature for 5 hours. 1.5 l of water are subsequently added thereto, the aqueous phase is separated, extracted twice with 250 ml of methylene chloride each time and acidified by the addition of 850 ml of 37 percent aqueous hydrochloric acid. After stirring at room temperature for 2 hours the suspension obtained is cooled to 0° C. and stirred for a further 0.5 hour. The precipitate is filtered off, washed in succession with 1000 ml of cold water, 1000 ml of methanol and 1000 ml of ether and dried at 40° C. for 12 hours in vacuo (1600 Pa). There is obtained (3S,4S)-3-μ(Z)-2-(2-amino-4-thiazolyl) 2-[(carboxymethoxy)imino]acetamido/-4-carbamoyloxymethyl-2-oxo-1-azetidinesulphoni̲c acid of m.p. 207° C.

EXAMPLE 5

11.66 g of the lithium salt of allyl 2-(2-amino-4-thiazolyl)-2-syn-hydroxyimino-acetate are suspended in 100 ml of dry tetrahydrofuran at room temperature, the suspension is treated with 6.2 ml of pivaloyl chloride, the mixture is stirred for 45 minutes, the solvent is evaporated off and the residue is partitioned between ethyl acetate and water. The aqueous phase is extracted a further twice with ethyl acetate. The combined organic phases are washed twice with saturated bicarbonate solution and in each case once with water and saturated sodium chloride solution, dried over magnesium sulphate and evaporated. The residue is recrystallized from t-butyl methyl ether and there is obtained allyl 2-(2-amino-4-thiazolyl)-2-syn-pivaloyloxyimino-acetate of m.p. 141°–143° C.

I claim:

1. A process for producing a compound of the formula

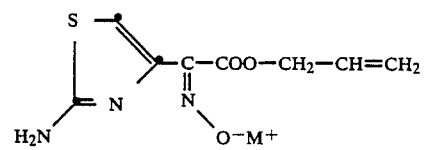

wherein M is an alkali metal atom, which process comprises:

(a) reacting allyl alcohol with at least about one molar equivalent of a base selected form the group consisting of alkali metal, alkali metal hydride, alkali metal alkyl, and alkali metal hydroxide to form a corresponding allyl alcohol salt of the formula $$CH_2=CH-CH_2-O^-M^+ \qquad III$$

wherein M has the above significance; and (b) reacting about one to about two molar equivalents of a compound of the formula

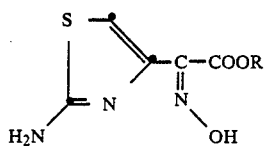 II whein R is lower alkyl,
with compound III under anhydrous conditions and in excess allyl alcohol thereby to produce compound I.

2. The process of claim 1, wherein M is a potassium atom.

3. The process of claim 1, wherein R is ethyl.

4. A process for producing a compound of the formula

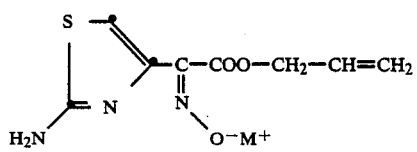 I wherein M is a potassium atom, which process comprises:
(a) reacting allyl alcohol with at least about one molar equivalent of a base selected form the group consisting of potassium, potassium, hydride, potassium alkyl, and potassium hydroxide to form a corresponding allyl alcohol salt of the formula $$CH_2=CH-CH_2-O^-M^+ \qquad III$$

wherein M has the above significance; and
(b) reacting about one to about two molar equivalents of a compound of the formula

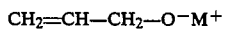

wherein R is lower alkyl,
with compound III under anhydrous conditions and in excess allyl alcohol thereby to produce compound I.

5. A process for producing a compound of the formula

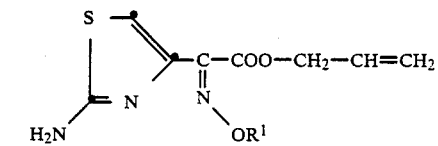 IV wherein $R^1$ is lower alkyl, lower alkanoyl, lower alkenyl, $-CH_2COOR^2$ or $-C(CH_3)_2COOR^2$, and $R^2$ is a readily cleavable group, which process comprises:
(a) reacting allyl alcohol with at least about one molar equivalent of a base selected form the group consisting of potassium, potassium hydride, potassium alkyl, and potassium hydroxide to form a corresponding allyl alcohol salt of the formula $$C_2=CH-CH_2-O^-M^+ \qquad III$$

wherein M is an alkali metal atom;
(b) reacting about one to about two molar equivalents of a compound of the formula

 II

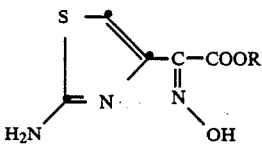

wherein R is lower alkyl,
with compound III under anhydrous conditions and in excess allyl alcohol to produce a compound of the formula

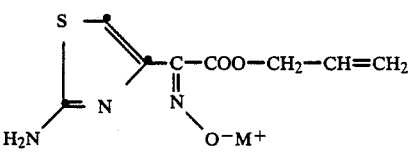 I wherein M is an alkali metal atom, and
(c) reacting compound I with a compound of the formula $$R^1-X \qquad V$$

wherein X is a leaving group and $R^1$ has the above significance, thereby to produce compound IV.

6. The process of claim 5, wherein X is halogen.

* * * * *